(12) United States Patent
Herslof et al.

(10) Patent No.: US 6,517,883 B1
(45) Date of Patent: Feb. 11, 2003

(54) SATIETY PRODUCT

(75) Inventors: Bengt Herslof, Stockholm (SE); Lars Lindmark, Falsterbo (SE); Karin Bohlinder, Solna (SE); Anders Carlsson, Stochholm (SE)

(73) Assignee: Scotia Holdings PLC, Stirling (GB)

( * ) Notice: Subject to any disclaimer, the term of this patent is extended or adjusted under 35 U.S.C. 154(b) by 0 days.

(21) Appl. No.: 09/462,330

(22) PCT Filed: Jul. 6, 1998

(86) PCT No.: PCT/SE98/01326

§ 371 (c)(1),
(2), (4) Date: Jan. 6, 2000

(87) PCT Pub. No.: WO99/02041

PCT Pub. Date: Jan. 21, 1999

(30) Foreign Application Priority Data

Jul. 7, 1997 (SE) .............................................. 9702630

(51) Int. Cl.⁷ .................................................. A23D 7/01
(52) U.S. Cl. ........................................... 426/602; 426/2
(58) Field of Search ............................ 426/601, 2, 804, 426/602; 514/909, 911

(56) References Cited

U.S. PATENT DOCUMENTS

| | | | | |
|---|---|---|---|---|
| 4,871,768 A | * | 10/1989 | Bistrian et al. ............. | 514/547 |
| 5,026,548 A | * | 6/1991 | Evans et al. ............. | 424/195.1 |
| 5,061,506 A | * | 10/1991 | Leach ......................... | 426/602 |
| 5,258,197 A | * | 11/1993 | Wheeler ..................... | 426/607 |
| 5,264,237 A | * | 11/1993 | Traitler et al. .............. | 426/611 |
| 5,336,514 A | * | 8/1994 | Jones et al. ................. | 426/564 |
| 5,688,528 A | * | 11/1997 | Carlsson et al. ............ | 424/450 |
| 5,698,254 A | * | 12/1997 | Campbell et al. ........... | 426/617 |
| 5,716,639 A | * | 2/1998 | Carlsson et al. ............ | 424/450 |
| 5,977,059 A | * | 11/1999 | Khoo et al. ................... | 514/2 |
| 5,994,295 A | * | 11/1999 | Khoo et al. ................... | 514/2 |

FOREIGN PATENT DOCUMENTS

| WO | WO 87/03198 | * | 6/1987 |
| WO | WO95/20943 | * | 8/1995 |
| WO | WO 97/11141 | * | 3/1997 |
| WO | WO99/020041 | * | 1/1999 |

OTHER PUBLICATIONS

Meyer, 1960. Food Chemistry. Reinhold Publishing Corp. New York. p. 63.*

* cited by examiner

Primary Examiner—Carolyn Paden
(74) Attorney, Agent, or Firm—Hoffman & Baron, LLP

(57) ABSTRACT

A food composition giving a prolonged feeling of satiety, comprising a mixture of or an oil-in-water emulsion of triglyceride oils having a solid fat content at ambient or body temperature with a food emulsifier. The invention also refers to the use of said mixture or oil-in-water emulsion for the preparation of a pharmaceutical composition for the control of calorie or fat intake.

9 Claims, No Drawings

SATIETY PRODUCT

The present invention refers to a mixture or an emulsion of a lipid with a polar lipid emulsifier which after ingestion gives an improved feeling of satiety and also results in reduced calorie and especially fat intake at a subsequent meal.

BACKGROUND OF THE INVENTION

Overweight and overeating are major health problems in the Western World. These, conditions are a result of an inbalance between energy intake and expenditure. One cause may be lack of appetite control.

It is well known that products with a high fat content, such as for instance cream, bring about a feeling of satiety. It would, however, be desirable to have a food product which provided a more rapid onset of such a feeling of satiety, which produced a feeling of satiety for a longer period of time or which produced the same feeling of satiety at a lower caloric intake. Also desirable would be a product which, when consumed, led to a reduced caloric intake at a later meal. Since fat is the most calorie-dense food, what would be especially desirable would be a product which selectively reduced fat intake.

PRIOR ART

EP 0 246 294 refers to an enteric preparation for the treatment of obesity. Said enteric preparation is a capsule, a tablet or microcapsules coated with a coating resistant to gastric juice which dissolves in the intestines. The enteric preparation contains specific hydrophobic substances which are said to give a reduced food intake when brought into contact with the distal part of the small intestine.

WO 95/20943 describes the use of DGDG-rich material, a galactolipid material, as an emulsifier in oil-in-water emulsions for pharmaceutical, nutritional and cosmetic use. The galactolipid material utilized in said applications was prepared from cereals by extraction of the lipids with ethanol and a subsequent purification on a chromatographic column to pure DGDG or a DGDG-rich fraction of polar lipids. The emulsion can be used as a carrier in pharmaceutical compositions as well as in nutritional, cosmetical, food and agricultural products.

WO 97/11141 describes a method for producing a fractionated vegetable oil which is characterized by containing 10–90% by weight of polar lipids, preferably 20–75%, and a remainder of non-polar lipids. The fractionated vegetable oil is preferably also characterized by containing more than 5% by weight, preferably more than 20%, glycolipids. Said fractionated vegetable oil also preferably contains more than 3% by weight, preferably more than 15% DGDG and consists of a wide range of polar and amphiphilic lipids in a continuous triglyceride phase. The fractionated vegetable oil can be used as a surface active agent for the formulation of a food, pharmaceutical, skin care or other product for oral, enteral, parenteral, topical or any other form of administration.

DESCRIPTION OF THE INVENTION

The present invention is related to the use of a mixture or an oil-in-water emulsion of a lipid as a food or for the formulation of a food composition giving a rapid, improved and prolonged feeling of satiety, reducing calorie intake at later meals and selectively producing a greater reduction in fat consumption.

The invention refers to a food composition giving a prolonged feeling of satiety, comprising a mixture of triglyceride oils having a solid fat content at ambient to body temperature and a food emulsifier.

The invention also refers to a food composition giving a prolonged feeling of satiety, comprising an oil-in-water emulsion of triglyceride oils having a solid fat content at ambient to body temperature with a food emulsifier in an aqueous solution.

The triglyceride oils of said mixtures or emulsions can be any triglyceride material having a solid fat content at ambient to body temperature. The triglyceride oils are defined by the percentage of solid fat content, determined by NMR serial measurements as described in IUPAC method no. 2.150, 7th edition. Triglyceride refers to triacylglycerol, that is glycerol esterified to three fatty acids.

The triglyceride oils are preferably selected from the group consisting of palm oil, cocoa butter or other confectionery fats. Further examples of triglyceride oils are illipe butter, shea butter, kokum butter, sal butter or other natural oils or fractions thereof with a similar solid fat content or melting range. Other examples of such oils are hydrogenated or partly hydrogenated soybean oil, rapeseed oil, cotton oil and sunflower oil or fractions thereof. The triglyceride oils may also be synthetic or semi-synthetic. Body temperature is the temperature of the healthy human or animal body.

The triglyceride oils should contain at least 90% by weight of triglycerides, preferably more than 95% by weight.

The invention especially refers to a food composition wherein the triglyceride oils are a fraction of palm oil. This fraction of palm oil is obtained from commercial palm oil, which is fractionated to specific mixtures of suitable triglycerides, based on the combination of mainly palmitic, oleic, linoleic and stearic esters of glycerol, respectively. Preferably the content of triglycerides in the palm oil fraction should be not less than 99% by weight. The purity can be checked by conventional chromatographic methods, such as thin-layer chromatography or high-performance liquid chromatography.

It seems to be of importance that the triglyceride oils utilised in the emulsion are very pure and free from minor components.

Food emulsifiers, that is emulsifiers commonly used in food applications are generally esters composed of a hydrophilic and a lipophilic part. In general, the lipophilic part is composed of stearic, palmitic, oleic, or linoleic acid or a combination of said fatty acids. The hydrophilic part is generally composed of hydroxyl, carboxyl, or oxyethylene groups. Examples of families of food-grade emulsifiers are lecithins, mono- and diglycerides, propylene glycol monoesters, lactylated esters, polyglycerol esters, sorbitan esters, ethoxylated esters, succinylated esters, fruit acid esters, acetylated mono- and diglycerides, phosphated mono- and diglycerides and sucrose esters. The emulsion of the triglyceride oils can also be obtained when the oils are mixed with suitable foods or food products, making use of the inherent emulsification properties of said foods or food products. Food emulsifiers according to the invention should be able to emulsify more than 20% by weight of the triglyceride oils, preferably more than 40% by weight, giving an emulsion which is still liquid in order to facilitate the processing of a food product in which the emulsion is incorporated.

A preferred emulsifier of the invention is lecithin, for instance produced from egg yolk, milk, soybean oil, sunflower oil, and rapeseed oil, which consists of a mixture of mainly phospholipids, such as phosphatidylcholine and phosphatidylethanolamine. Lecithin refers in this context to crude mixtures of said phospholipids which are obtained on degumming of the starting materials, and which are commercially available as food emulsifiers.

Another preferred emulsifier is a galactolipid based emulsifier. Galactolipids belong to the group of glycolipids, well known constituents of plant cell membranes. The most important classes of these contain one to four sugars linked glycosidically to diacyiglycerol. The two most abundant classes contain one and two galactose units, respectively, and the commonly used nomenclature and abbreviations of these are mono- and digalactosyldiglyceride, MGDG and DGDG, sometimes referred to as galactolipids. Galactolipids, primarily DGDG and DGDG-rich materials, have been investigated and found to be a surface active material of interest in industrial applications such as food, cosmetics, and pharmaceutical products. Galactolipid emulsifiers are described in WO 95/20943 and WO 97/11141.

The invention also refers to a food product wherein the triglyceride oils are combined with other lipids containing essential fatty acids. Essential fatty acids are polyunsaturated acids of the (n-6) and (n-3) families which are essential for life and good health. The other lipids containing essential fatty acids can be derived from vegetable oils of all types, such as oils from the seeds and beans of soybean, sunflower, safflower, cottonseed, rapeseed (canola), palm, palmkernel, coconut, corn, evening primrose, borage, groundnut, sesame, and similar, furthermore animal oils and fats such as fish oils, liver oils, egg oils, and similar, obvious to a person skilled in the art, which in combination with the triglycerides can be emulsified by the emulsifiers of the invention.

A preferred aspect of the invention is a food composition wherein the triglyceride oils of the invention are combined with palmkernel oil or coconut oil, giving in addition to a prolonged feeling of satiety also a rapid onset of satiety.

The invention also refers to a food composition wherein the qalactolipid based emulsifier is a fractionated oat oil.

Oil-in-water emulsions refer in this application in addition to liquid oil dispersions also to solid fat dispersions, that is suspensions.

Oil-in-water emulsions are prepared by using the emulsifier either alone or in combination with other amphiphilic compounds, such as co-surfactants. The oil-in-water emulsion may also comprise optional additives known in the art for improving different aspects of the composition, such as flavouring agents, sweeteners, colorants, thickening agents, preservatives, antioxidants, etc.

Oil-in-water emulsions are prepared by conventional methods. For example, a 30wt % emulsion of a triglyceride oil in water is prepared by adding the emulsifier to the liquid triglyceride. The continuous phase may be pure water or an aqueous solution containing water-soluble additives such as isotonic agents, sweeteners, flavours, and preservatives. If necessary, the pH of the aqueous phase is then adjusted. The oil phase as well as the aqueous phase are preheated and then the oil phase is added to the aqueous phase under high-shear mixing. The pre-emulsion is then subjected to high-pressure homogenisation.

The oily mixture consisting of the triglyceride oils plus the emulsifier may be added to solid or semi-solid foods, which then become naturally emulsified to an oil-in-water emulsion on exposure to the fluids of the gastrointestinal tract. The oily mixture may also contain oil-soluble additives such as antioxidants and flavours. The oily mixture may also be made into a ready-prepared emulsion which can be added to liquid or semi-liquid foods and drinks.

The invention especially refers to a food composition wherein the mixture of triglyceride oils and emulsifier or the oil phase of the emulsion comprises 80–99% by weight of the triglycerides and 1–20% by weight of emulsifier.

It should be emphasized that the emulsifying capacity of the emulsifier depends on the composition of the emulsifier. The fractionated oat oil mentioned above can without further purification be used as an emulsifier in an amount of 1–20% by weight of the total composition for preparing oil-in-water emulsions of 5–60% by weight of triglycerides. The galactolipid emulsifier of WO 95/20943 should be used in 0.1–5.0% by weight of the total composition for preparing oil-in-water emulsions of 5–80% by weight of triglycerides.

The invention also refers to the use of a mixture of triglyceride oils having a solid fat content at ambient to body temperature and a food emulsifier or an oil-in-water emulsion thereof as a food or for the preparation of a food composition giving a prolonged feeling of satiety, as well as a reduction in calorie intake and especially a selective reduction in fat intake at subsequent meals. The satiety effect is most noticeable during the period 3–4 h after intake.

The emulsion or the oily mixture can be used in formulation of dairy products, ice cream, margarines, spreads, salad oils and dressings, processed meat products, confectionery, fillings, sauces, soups, fruit drinks, desserts, baby foods, but also nutritional and pharmaceutical supplements. Especially the oily mixture can be used in solid or semi-solid foods such as chocolates, other candies, baked goods and any other appropriate foods.

The invention also refers to a dairy product comprising 1–30% by weight, preferably 2–15% by weight of the oil-in-water emulsion. A preferred dairy product, such as a yogurt, comprises 4–10% by weight of an emulsion of a triglyceride fraction of palm oil and fractionated oat oil.

In order to obtain a prolonged feeling of satiety a 40 wt % emulsion should be taken in an amount of 1–200 ml per serving or meal, preferably 5–100 ml and very preferably 10–30 ml. The oil component alone, that is the oily mixture, may be used in proportionally smaller quantities.

The invention also refers to a mixture of triglyceride oils having a solid fat content at ambient to body temperature and a food emulsifier or an oil-in-water emulsion thereof for the preparation of an oral pharmaceutical composition for the prophylaxis and treatment of obesity, for the control of calorie or fat intake and for the prevention and treatment of cardiovascular diseases and diabetes.

The invention also refers to the use of an oil-in-water emulsion of triglyceride oils having a solid fat content at ambient to body temperature with a food emulsifier for the preparation of a pharmaceutical composition for the prophylaxis and treatment of obesity, for the control of calorie or fat intake and for the prevention and treatment of cardiovascular diseases and diabetes.

When used in a pharmaceutical composition for weight reduction, control of calorie intake or the prevention or treatment of any appropriate disease, such as cardiovascular disease or diabetes, the composition can in addition to the oil-in-water emulsion comprise another therapeutically active substance.

In the following Examples and Tests different lipids and emulsifiers have been formulated into mixtures and emulsions and tested as to effect on satiety and food consumption. The following fats or oils have been used: Akofrite (trade name for a palm oil from Karlshamns, Karlshamn, Sweden); Fractionated palm oil (CPL®-Palm oil, Scotia LipidTeknik, Stockholm, Sweden) obtained by fractionation of Akofrite; palmkernel oil; corn oil; and Fractionated soybean oil (CPL®-Soybean oil, Scotia LipidTeknik, Stockholm, Sweden). As emulsifiers have been used Fractionated oat oil (Scotia LipidTeknik, Stockholm, Sweden) comprising about 20% DGDG, and prepared from oats in accordance with WO 97/11141; Galactolipids (CPL®-Galactolipids, Scotia LipidTeknik, Stockholm, Sweden) comprising about 60% DGDG, and prepared from oats in accordance with WO 95/20943; soybean lecithin; and soybean phosphatidylcholine.

The Fractionated palm oil used has the following fatty acid composition as determined by means of gas-liquid chromatography after alkaline methanolysis: 40–45 wt % palmitic acid, 38–42 wt % oleic acid, 8–10 wt % linoleic acid, and 4–5 wt % stearic acid, the remainder being lauric acid, myristic acid, arachidic acid and palmitoleic acid.

The Fractionated palm oil has a triglyceride (TG) content of 99.8–100.0 wt %, a solid fat content at 20 and 35° C. ($N_{20}$ and $N_{35}$) of 31 and 6%, respectively. The other tested oils have the following corresponding data: Akofrite: TG=96 wt %, $N_{20}$=28%, and $N_{35}$=5%; Palmkernel oil: TG=96 wt %, $N_{20}$=40% and $N_{35}$=0%; Fractionated soybean oil: TG=99.5 wt %, $N_{20}$=0% and $N_{35}$=0%; corn oil: TG=97 wt %, $N_{20}$=0% and $N_{35}$=0%.

EXAMPLES

Example 1

Emulsion giving a Prolonged Satiety

Preparation of 40 wt % emulsions with Fractionated palm oil (batch size 300 g).

| Ingredients | wt % |
| --- | --- |
| Water | 58.0 |
| Fractionated palm oil | 40.0 |
| Fractionated oat oil | 2.0 |

The palm oil is melted at 50° C. and mixed with the Fractionated oat oil. The oil phase and the water are preheated to 65–70° C. and then the oil phase is added to the water under high-shear mixing at 15,000 rpm for 4 min. The pre-emulsion is then divided into two parts; one part is homogenized at 400 bar, the other part at 800 bar, both for 6 cycles at 60° C. (Rannie homogenizer, Model Mini-Lab 8.30 H, APV Rannie, Denmark). Both parts of the preparation result in emulsions with a similar cream-like consistency. The average particle size (Z average) is in both cases around 480 nm (Zetasizer 4, Malvern Instruments, UK).

An emulsion prepared as above (Olibra®, Scotia LipidTeknik, Stockholm, Sweden) can be stored at 2–8° C. until being used as an ingredient in the production of a food product. The Olibra® emulsion can be used as an ingredient in the manufacturing of a yogurt product. A yogurt containing 6–7% Olibra® is today marketed as Mäväl® (Skånemejerier, Lunnarp, Sweden).

Example 2

Emulsion Giving a Prolonged Satiety

| Ingredients | wt % |
| --- | --- |
| Water | 58.0 |
| Fractionated palm oil | 40.0 |
| Galactolipids | 2.0 |

The palm oil is melted at 50° C. and mixed with the Galactolipids. The oil phase and the water are preheated to 65–70° C. and then the oil phase is added to the water under high-shear mixing at 15,000 rpm for 4 min. The pre-emulsion is homogenised at 800 bar, for 6 cycles at 60° C. (Rannie homogenizer, Model Mini-Lab 8.30 H, APV Rannie, Denmark). This results in an emulsion with a creamy consistency, with an average particle size (Z average) of 290 nm (Zetasizer 4, Malvern Instruments, UK). At a high Galactolipids content (more than 5%) a thick paste is formed.

Example 3

Emulsion Giving a Prolonged Satiety

| Ingredients | wt % |
| --- | --- |
| Water | 50.5 |
| Fractionated palm oil | 47.0 |
| Fractionated oat oil | 2.5 |

The palm oil is melted at 50° C. and mixed with the Fractionated oat oil. The oil phase and the water are preheated to 65–70° C. and then the oil phase is added to the water under high-shear mixing at 15,000 rpm for 2 min. The pre-emulsion is then homogenised at 600 bar, for 5 cycles at 60° C. (Rannie homogenizer, Model Mini-Lab 8.30 H, APV Rannie, Denmark). This results in an emulsion with a cream-like consistency. The average particle size (Z average) is ≈400 nm (Zetasizer 4, Malvern Instruments, UK).

Example 4

Emulsion Giving a Rapid and Prolonged Satiety

| Ingredients | wt % |
| --- | --- |
| Water | 58 |
| Palmkernel oil | 20 |
| Fractionated palm oil | 20 |
| Fractionated oat oil | 2 |

The palmkernel oil is mixed with the Fractionated palm oil and melted at 65° C. and then mixed with the Fractionated oat oil. The water is preheated to 65–70° C. and then the oil phase is added to the water under high-shear mixing at 15,000 rpm for 10 min. The pre-emulsion is, then homogenised at 600 bar, for 4 cycles at 60° C. (Rannie homogenizer, Model Mini-Lab 8.30 H, APV Rannie, Denmark). This resulted in an emulsion with a cream-like consistency. The average particle size (Z average) is ≈400 nm (Zetasizer 4, Malvern Instruments, UK).

Example 5
Ice Cream

| Ingredients |
| --- |
| 2 eggs |
| 125 ml sugar |
| 250 ml milk |
| 5 g orange-cocoa aroma |
| 200 ml Olibra ® |

Eggs, sugar and milk are mixed and slowly boiled whilst whipping until the cream thickens. Then the cream is mixed with about 5 g orange-cocoa aroma (from NorrMejerier, Luleå, Sweden) and cooled to room temperature. 200 ml Olibra® is added and the mixture is the poured into an ice cream machine and run for about 30 minutes.

Example 6
Carrot Cake

| Ingredients |
| --- |
| 4 eggs |
| 250 ml Fractionated palm oil + Fractionated oat oil |
| 600 ml grated carrot |
| 200 ml brown sugar |
| 150 ml sugar |
| 1 teaspoon baking soda |
| 1 teaspoon salt |
| 3 teaspoons cinnamon |
| 450 ml wheat flour |

The eggs and the mixture (40:2 by weight) of Fractionated palm oil and Fractionated oat oil are added to the grated carrots and the mixture obtained is whipped by an electric mixer.

All the dry ingredients are mixed and gently stirred into the carrot mixture. The batter is poured into a high, oiled and breaded baking-tin and heated for 60 minutes at an oven temperature of 175° C.

TESTS

Test 1
Effect of Emulsion on Satiety

In order to evaluate the effect on satiety, the emulsion prepared in Example 1 at 800 bar was compared to dairy double cream containing 40.0 wt % milk fat, that is the same fat content as Olibra®. 25 ml of the emulsion or the cream were given to five human volunteers instead of a meal at lunch time and swallowed together with 200 ml drinking water. No food or drink was allowed during the following 3 hours. The feeling of satiety or fullness was evaluated every 15 minutes during the first hour and then every 30 minutes using a 100 mm VAS scale (Br. J. Nutr. (1995) 74, 427–436). A value of 100 means a complete satiety and a value of 0 extreme hunger. The results are given in the following table.

TABLE 1

| Satiety (mm VAS scale) | | | | | | | | | |
| --- | --- | --- | --- | --- | --- | --- | --- | --- | --- |
| Time (min) | 0 | 15 | 30 | 45 | 60 | 90 | 120 | 150 | 180 |
| Emulsion | 15 | 55 | 85 | 90 | 88 | 81 | 74 | 66 | 58 |
| Cream | 18 | 43 | 71 | 73 | 69 | 65 | 56 | 47 | 39 |

The result show that the emulsion of the invention had a surprising and significantly better effect (<0.05 in paired Student's t test) on satiety compared to the cream. The satiety effect was 20–45% higher with the emulsion, it was more rapid in onset and lasted longer.

Test 2
Stability of Different Emulsions in Gastric Juice

In order to test the stability of emulsions prepared from different oil fractions and different emulsifiers in a simulated gastric environment the following experiment was performed.

An emulsion was prepared from 40% by weight oil or fat, 2% by weight emulsifier and 58% by weight water and homogenised at 800 bar in the same way as stated in Example 1. The oils tested were, in addition to the Fractionated palm oil (PO), Akofrite, that is the non fractionated palm oil, and corn oil (CO). The emulsifiers were, in addition to the Fractionated oat oil, soybean lecithin (s-lecithin), and soybean phosphatidylcholine (s-PC).

Artificial gastric juice, pH ≈1, (prepared by dissolving 2.0 g of sodium chloride and 3.2 g of pepsin powder in water, adding 1 M hydrochloric acid and diluting to 1000 ml with water) was added in an amount of 250 ml to a thermostated 500 ml beaker and heated to 37° C. under magnetic stirring at 200 rpm. 12.5 g of the dispersion to be tested was added and the mixture obtained was observed as to appearance after 1 and 30 minutes, respectively.

TABLE 2

| Emulsion stability in gastric juice | | |
| --- | --- | --- |
| | Appearance after | |
| Emulsion | 1 min | 30 min |
| Olibra ® | Large fluffy aggregates (flocs) on the surface | Same appearance |
| PO/s-PC | Homogeneous emulsion, fine drops | Same appearance |
| CO/Fractionated oat oil | Oil phase on top, large droplets | Same appearance |
| PO/s-lecithin | Large dense aggregates on the surface | Same appearance |
| Akofrite/ Fractionated oat oil | Oil separation on the surface | Solid fat on the surface |

The results show the different behaviour between emulsions based on oils that are liquid, or semi-solid or solid, at 20–37° C., or prepared by means of different emulsifiers. When an emulsion based on Fractionated palm oil and a Fractionated oat oil or soybean lecithin is added to warm artificial gastric juice, large fluffy aggregates or flocs are precipitated. Such an aggregate formation gives rise to a large specific area of the dispersed fat. The aggregates retain their physical integrity at body temperature for a long time without being transformed to oil droplets, that is no coalescence occurs. For a food product containing the emulsion, such as a yogurt, this may lead to a longer residence time of the fat in the GI tract. An emulsion based on corn oil, which is liquid at ambient as well as body temperature, as well as on Akofrite having a solid fat content at the respective temperatures, although emulsified with the Fractionated oat oil, leads to the formation of large oil droplets which consequently have a smaller specific area. In the same way an emulsion based on the Fractionated palm oil, but emulsified with the conventional emulsifier soybean phosphatidylcholine will not produce any flocs in warm gastric juice but only fine oil droplets.

Test 3
Effect of Yogurt Containing Different Fat Emulsions on Satiety

In this test different fat emulsions were incorporated into a yogurt and the effect on satiety evaluated. The emulsions were based on those emulsifiers which in Test 2 gave the preferred floc formation in gastric juice, that is Fractionated oat oil and soybean lecithin, and the lipids tested were in addition to the Fractionated palm oil also Akofrite, Fractionated soybean oil and palmkernel oil.

Yogurt products were prepared ex tempore by mixing 12.5 g of the different emulsions stated below with 187.5 g of a commercial low fat yogurt, Lätt-Yoggi (Arla, Stockholm, Sweden) giving a yogurt having a fat content of 3 wt %. A conventional 3 wt % fat yogurt, Yoggi (Arla, Stockholm, Sweden) was used as placebo.

The following emulsions 1–5 were prepared in the same way as stated in Example 1, after homogenisation at 800 bar:

| | |
|---|---|
| 1 | Fractionated palm oil + Fractionated oat oil |
| 2 | Fractionated palm oil + soybean lecithin |
| 3 | Fractionated soybean oil + Fractionated oat oil |
| 4 | Akofrite + soybean lecithin |
| 5 | Palmkernel oil + Fractionated oat oil |

Two different tests with 8 and 11, respectively, healthy subjects were performed. The degree of satiety was calculated in the same way as in Test 1 above.

In the first test the subjects had 200 ml yogurt, 200 g lettuce, 1 tomato and 50 g carrot or, in addition to the yogurt, 2 pieces of hard bread or 1 piece of soft bread for lunch. The results are given in the following Table 3.

TABLE 3

Satiety after having a yogurt meal for lunch

| Yogurt with emulsion number | Satiety at the start | Satiety 1 h after intake | Satiety 4 h after intake | SI score |
|---|---|---|---|---|
| 1 | 12 | 66 | 30* | 138* |
| 2 | 17 | 65 | 28* | 128* |
| 3 | 19 | 62 | 20 | 112 |
| 4 | 20 | 63 | 24 | 118 |
| 5 | 18 | 75 | 19 | 125 |
| Placebo | 15 | 68 | 18 | 108 |

*significant

From the values obtained it is obvious that the initial satiety was about the same for all tested products. Palmkernel oil, however, gave the most rapid onset of the satiety. 4 hours after intake the yogurt with emulsion no. 1, and optionally no. 2, seem to be superior as to satiety as well as SI score. SI stands for Satiety Index, as defined in the Eur. J. Clin. Nutr. (1995) 49, 675–690. The SI score is the cumulative value of satiety during the complete test period (4 h).

In the second test the subjects had a normal lunch not than 12 o'clock and a yogurt product as a snack at 2 o'clock in the afternoon, giving an interval of 2 hours between the meals.

The results of this second test are given in the following Table 4. In this test the hunger is evaluated, the value 0 expressing a complete satiety and the value 100 describing extreme hunger.

TABLE 4

Hunger after a yogurt snack meal in the afternoon

| Yogurt with emulsion number | Hunger after 1 h | Hunger after 4 h |
|---|---|---|
| 1 | 17 | 38* |
| 2 | 19 | 43* |
| 3 | 19 | 56 |
| 4 | 20 | 49 |
| 5 | 13 | 48 |
| Placebo | 18 | 60 |

*significant

This test is more difficult to perform as the previous intake of lunch often is dominating. This is the reason why hunger instead of satiety has been tested, also giving an evaluation of the snacking behaviour. The yogurt product giving the lowest hunger value 4 hours after intake is the yogurt with emulsion no. 1, which in addition to the yogurt with emulsion no. 2, give a significantly decreased hunger value. As in the first test palmkernel oil gave the quickest onset of the satiety.

Test 4
Effect of Yogurt Containing Olibra® on Energy Intake

In this study the effects of the consumption at lunch of yogurt containing 5 g of the fat emulsion prepared in Example 1 and a control yogurt containing milk fat, respectively, on the subsequent intake of energy and macronutrients, were evaluated.

Subjects and Methods

Two studies were conducted over the periods October–December 1997 and February–March 1998. The subjects were drawn from students and staff at the University of Ulster, Coleraine. Subjects were asked to refrain from moderate to heavy exercise on the day preceding, and on the day of each study. In Study 1 there were 30 subjects (15 women and 15 men) and in Study 2, 30 subjects (16 women and 14 men). Exclusion criteria were body mass index (BMI, $kg/m^2$) over 30, smokers, vegetarians and those taking any prescription medication. The studies were approved by the Research Ethical Committee of the University of Ulster, and were carried out in the Metabolic Suite of the University. Before the study weight, height and percentage of body fat (bioelectrical impedance Bodystat 1500) were measured. The design of each study was a randomised double-blind crossover over two separate days, on the same day of the week, and with one week interval between crossover. Subjects were asked to fast from 20.00 h on the evening preceding the days of the study, and participation was conditional upon confirmation that subjects had complied. At 9.00 h on each study day, subjects consumed the same defined breakfast. This provided 25% of estimated energy expenditure (calculated as 1.4 times estimated baal metabolic rate (Schofield 1985)). Macronutrient composition, as percentage of energy, was carbohydrate 46, fat 37 and protein 17. Subjects then followed their normal routine until 13.00 h when they received 200 g portions (in plain white containers) of the test or control yogurt in random order. Both yogurts had the same energy and macronutrient composition, that is 800 kJ, 6.8 g protein, 28.8 g carbohydrate per portion, and had similar sensory characteristics. However, the control yogurt contained only milk fat, whilst in the test yogurt 5 g of milk fat was replaced by 5 g Olibra®. The test and the control yogurts were supplied by Skanemejerier, Lunnarp, Sweden. After consuming the yogurt, subjects resumed their normal routine for the afternoon, during which period they were instructed not to consume anything other than water, if required. At 17.00 h subjects returned to the Metabolic Suite and were given ad libitum access to a wide range of familiar sweet and savoury foods. All foods were weighed prior to the meal, and all uneaten food was weighed after the meal. Intake was assessed by difference. For the remainder of the day the subjects were permitted to eat and drink as they wished but were asked to keep a weighed food record of all items of food or drink consumed. Energy and macronutrient intakes were assessed using Compeat 4.0. Data are presented as means ±SEM. Comparisons were performed by use of paired t tests with all subjects and for male and female groups.

Results

The results of the test are given in the following Tables 5 and 6.

For all subjects and for the females as a separate group there were significant reductions in energy intake following the consumption of the test yogurt in both studies, see Table 5 below. For the males there were reductions in energy intake, but this was only significant in study 2. In studies 1 and 2, respectively, the total energy intakes following yogurt consumption for all subjects were 15.9% and 12.6% lower. For females energy intakes were 22.0% and 14.6% lower and for the males 10.4% and 10.9% lower.

In both studies more subjects recorded that no food had been consumed after the evening meal following the test yogurt, see Table 6. Overall the mean intakes following the evening meal were low. Nevertheless the energy intakes were significantly lower following the test yogurt for all subjects and for the male group.

The fact that the reduction in intake was larger among the females may reflect the lower bodyweight of the female subjects which resulted in higher levels of Olibra® consumed by kg of body weight. On this basis females actually received a 20.2% greater dose than the males.

TABLE 5

Mean (SEM) intake at evening meal following test and control yoghurt lunches

| | All subjects | | Females | | Males | |
| --- | --- | --- | --- | --- | --- | --- |
| | study 1 (n = 29) | study 2 (n = 30) | study 1 (n = 15) | study 2 (n = 16) | study 1 (n = 14) | study 2 (n = 14) |
| Energy (MJ) | | | | | | |
| Test | 6.41* (0.49) | 6.87* (0.36) | 5.26* (0.43) | 5.62* (0.36) | 7.66 (0.78) | 8.30* (0.38) |
| Control | 7.62 (0.33) | 7.86 (0.36) | 6.74 (0.35) | 6.58 (0.31) | 8.55 (0.46) | 9.32 (0.41) |
| Fat (g) | | | | | | |
| Test | 70.4** (6.17) | 72.0** (4.95) | 58.1* (5.90) | 55.2* (4.39) | 83.5* (10.2) | 91.1* (6.24) |
| Control | 91.0 (4.80) | 84.7 (5.17) | 80.0 (5.01) | 68.5 (4.45) | 103 (7.22) | 103 (7.23) |
| Protein (g) | | | | | | |
| Test | 58.3* (4.75) | 69.2* (5.06) | 48.8 (5.14) | 52.9* (5.37) | 68.5 (7.39) | 88.0 (5.82) |
| Control | 67.0 (4.49) | 78.9 (4.72) | 58.0 (3.99) | 65.5 (4.19) | 75.9 (7.64) | 94.3 (7.02) |
| CHO (g) | | | | | | |
| Test | 177 (12.6) | 187* (7.80) | 142* (10.7) | 168* (9.32) | 214 (19.3) | 209 (10.3) |
| Control | 196 (10.0) | 204 (7.51) | 174 (13.6) | 184 (9.13) | 220 (11.4) | 228 (8.94) |

*$p < 0.05$,
**$p < 0.01$,
***$p < 0.001$ (2-tail) indicates test yogurt significantly different from control yogurt.

TABLE 6

Number of subjects consuming food after evening meal, and the mean (SEM) energy intakes after evening meal following test and control yogurt lunches.

| | All Subjects | | Females | | Males | |
| --- | --- | --- | --- | --- | --- | --- |
| | study 1 | study 2 | study 1 | study 2 | study 1 | study 2 |
| Test | | | | | | |
| C | 14 | 16 | 7 | 10 | 7 | 6 |
| N | 15 | 14 | 8 | 6 | 7 | 8 |
| Control | | | | | | |
| C | 20 | 23 | 9 | 13 | 11 | 10 |
| N | 9 | 13 | 6 | 3 | 3 | 4 |
| Energy (MJ) | | | | | | |
| Test | 0.68* (0.2) | 0.48** (0.1) | 0.61* (0.3) | 0.55* (0.2) | 0.80** (0.3) | 0.41* (0.2) |
| Control | 1.15 (0.3) | 0.67 (0.1) | 0.85 (0.3) | 0.85 (0.2) | 1.47 (0.5) | 0.89 (0.3) |

*$p < 0.05$,
**$p < 0.01$, (2-tail)
C: number of subjects consuming food after evening meal,
N: number of subjects not consuming anything after evening meal

What is claimed is:

1. A food composition capable of giving a prolonged feeling of satiety and giving a rapid onset of satiety, comprising an oil-in-water emulsion of triglyceride oil, said emulsion comprising water, a triglyceride containing oil which is at least partially solid at ambient to body temperature and which contains at least 90 wt. % triglycerides, and a galactolipid based food emulsifier, wherein the triglyceride containing oil is combined with palmkernel oil.

2. A food composition according to claim 1, wherein the galactolipid based emulsifier is a fractionated oat oil.

3. A food composition according to claim 1, wherein the oil phase of the emulsion comprises 80–90% by weight of the triglyceride containing oil and 1–20% by weight of the emulsifier.

4. A food composition according to claim 1, wherein the triglyceride containing oil has a purity of at least about 95 wt. % triglycerides.

5. A food composition according to claim 1, wherein said partially solid triglyceride containing oil has a solid fat content at ambient to body temperature.

6. A food composition capable of giving a prolonged feeling of satiety, comprising an oil-in-water emulsion of triglyceride oil, said emulsion comprising water, a triglyceride containing oil which is at least partially solid at ambient to body temperature and which contains at least 90 wt. % triglycerides, and a galactolipid based food emulsifier, wherein the triglyceride containing oil is selected from the group consisting of palm oil, cocoa butter, other confectionery fats and mixtures thereof.

7. A food composition according to claim 6, wherein the triglyceride containing oil is a fraction of palm oil.

8. A dairy product comprising 1–30% by weight of an oil-in-water emulsion, said emulsion comprising water, a triglyceride containing oil which is at least partially solid at ambient to body temperature and which contains at least 90 wt. % triglycerides, and a galactolipid based food emulsifier, wherein said dairy product comprises 4–10% by weight of an emulsion, said emulsion comprising water, a triglyceride fraction of palm oil and fractionated oat oil.

9. A dairy product according to claim 8, comprising 2–15% by weight of said emulsion.

* * * * *

UNITED STATES PATENT AND TRADEMARK OFFICE
CERTIFICATE OF CORRECTION

PATENT NO.    : 6,517,883 B1
DATED         : February 11, 2003
INVENTOR(S)   : Herslof et al.

It is certified that error appears in the above-identified patent and that said Letters Patent is hereby corrected as shown below:

Column 9,
Line 60, now reads "normal lunch not than" should read -- normal lunch not later than --

Column 12,
Table 6, line 14, now reads:

"Control 1.15 (0.3) 0.67 (0.1) 0.85 (0.3) 0.85 (0.2) 1.47 (0.5) 0.89 (0.3)" should read
-- Control 1.15 (0.3) 0.87 (0.1) 0.85 (0.3) 0.85 (0.2) 1.47 (0.5) 0.89 (0.3) --

Signed and Sealed this

Second Day of September, 2003

JAMES E. ROGAN
*Director of the United States Patent and Trademark Office*